United States Patent
Prince et al.

(10) Patent No.: US 7,407,570 B2
(45) Date of Patent: Aug. 5, 2008

(54) DISPOSABLE, SELF-ADMINISTERED ELECTROLYTE TEST

(75) Inventors: Jennifer Ryan Prince, Stoneham, MA (US); Andrew Dineen, Melrose, MA (US); John R. Williams, Lexington, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 252 days.

(21) Appl. No.: 10/388,198

(22) Filed: Mar. 13, 2003

(65) Prior Publication Data
US 2003/0201192 A1 Oct. 30, 2003

Related U.S. Application Data

(60) Provisional application No. 60/364,213, filed on Mar. 13, 2002.

(51) Int. Cl.
*G01N 27/333* (2006.01)

(52) U.S. Cl. .................. 205/792; 205/789; 204/416

(58) Field of Classification Search ......... 204/416–418, 204/409, 411; 205/775, 789, 789.5, 787, 205/792; 422/82.01, 82.03, 58
See application file for complete search history.

(56) References Cited

U.S. PATENT DOCUMENTS

| | | |
|---|---|---|
| 3,923,626 A | 12/1975 | Niedrach et al. |
| 3,923,627 A | 12/1975 | Niedrach et al. |
| 3,926,766 A | 12/1975 | Niedrach et al. |
| 3,957,613 A | 5/1976 | Macur |
| 4,062,750 A | 12/1977 | Butler |
| 4,214,968 A | 7/1980 | Battaglia et al. |
| 4,250,010 A | 2/1981 | Kondo et al. |
| 4,437,970 A | 3/1984 | Kitajima et al. |
| 4,517,291 A | 5/1985 | Seago |
| 4,549,951 A | 10/1985 | Knudson et al. |
| 4,552,625 A | 11/1985 | Van Der Velden |
| 4,654,127 A | 3/1987 | Baker et al. |
| 4,684,445 A | 8/1987 | Seshimoto et al. |
| 4,713,165 A | 12/1987 | Conover et al. |
| 4,772,377 A | 9/1988 | Geist et al. |
| 4,797,191 A | 1/1989 | Metzner et al. |
| 4,808,292 A | 2/1989 | Kessler et al. |
| 4,816,118 A | 3/1989 | Oyama et al. |
| 4,818,361 A | 4/1989 | Burgess et al. |
| 4,874,500 A | 10/1989 | Madou et al. |
| 4,882,544 A * | 11/1989 | Uekusa et al. ............ 324/511 |

(Continued)

FOREIGN PATENT DOCUMENTS

JP 56166461 12/1981

(Continued)

OTHER PUBLICATIONS

JPO English language computer translation of Kugimiya et al. (JP 2000206077 A) patent published Jul. 28, 2000.*

(Continued)

*Primary Examiner*—Alex Noguerola
(74) *Attorney, Agent, or Firm*—Goodwin Procter LLP

(57) ABSTRACT

A disposable, self-administered electrolyte test is affixed to the label of a commercially available electrolyte supplement, is available in the pharmacy section of a retail store, or is distributed by a physician or a clinic.

16 Claims, 11 Drawing Sheets

U.S. PATENT DOCUMENTS

| | | | |
|---|---|---|---|
| 4,959,130 A | | 9/1990 | Josowics et al. |
| 4,995,402 A | | 2/1991 | Smith et al. |
| 5,004,583 A | | 4/1991 | Guruswamy et al. |
| 5,046,496 A | | 9/1991 | Betts et al. |
| 5,047,044 A | | 9/1991 | Smith et al. |
| 5,105,338 A | * | 4/1992 | Held ............................ 361/683 |
| 5,112,455 A | | 5/1992 | Cozzette et al. |
| 5,183,549 A | | 2/1993 | Joseph et al. |
| 5,186,808 A | | 2/1993 | Yamaguchi et al. |
| 5,194,133 A | | 3/1993 | Clark et al. |
| 5,223,124 A | | 6/1993 | Ege |
| 5,234,568 A | * | 8/1993 | Tomita ........................ 204/416 |
| 5,250,168 A | | 10/1993 | Tsukada et al. |
| 5,312,590 A | | 5/1994 | Gunasingham |
| 5,336,388 A | | 8/1994 | Leader et al. |
| 5,393,401 A | | 2/1995 | Knoll |
| 5,397,451 A | * | 3/1995 | Senda et al. ............. 204/403.1 |
| 5,421,981 A | | 6/1995 | Leader et al. |
| 5,425,361 A | | 6/1995 | Fenzlein et al. |
| 5,431,800 A | | 7/1995 | Kirchhoff et al. |
| 5,468,374 A | | 11/1995 | Knoll |
| 5,505,836 A | | 4/1996 | Miyahara et al. |
| 5,545,303 A | | 8/1996 | Schasfoort et al. |
| 5,584,979 A | | 12/1996 | Lewenstam et al. |
| 5,678,695 A | * | 10/1997 | Ridgeway et al. ........... 206/583 |
| 5,700,360 A | | 12/1997 | Chan et al. |
| 5,804,049 A | | 9/1998 | Chan |
| 5,837,454 A | | 11/1998 | Cozzette et al. |
| 5,840,168 A | | 11/1998 | Chaniotakis et al. |
| 5,865,972 A | | 2/1999 | Buffle et al. |
| 5,911,862 A | | 6/1999 | Chan |
| 6,030,827 A | | 2/2000 | Davis et al. |
| 6,060,327 A | | 5/2000 | Keen |
| 6,083,710 A | | 7/2000 | Heller et al. |
| 6,121,009 A | | 9/2000 | Heller et al. |
| 6,123,820 A | | 9/2000 | Bergkuist et al. |
| 6,146,510 A | | 11/2000 | Leader et al. |
| 6,203,758 B1 | | 3/2001 | Marks et al. |
| 6,251,246 B1 | | 6/2001 | Chan |
| 6,284,478 B1 | | 9/2001 | Heller et al. |
| 6,436,055 B1 | * | 8/2002 | Roe ........................... 600/584 |
| 6,564,079 B1 | * | 5/2003 | Cory et al. .................. 600/393 |

FOREIGN PATENT DOCUMENTS

| | | | |
|---|---|---|---|
| JP | 61269056 | | 11/1986 |
| JP | 11-083797 A | * | 3/1999 |
| JP | 2000-206077 A | * | 7/2000 |

OTHER PUBLICATIONS

JPO English language computer translation of JP 11-083797 A; application published Mar. 26, 1999.*

"Solid-State Ion-Selective Electrode Arrays" by A. Lynch et al., Biomedical Environmental Sensor Technology Center, Dublin City University, Dublin, Ireland, Electroanalysis (1998), 10(16), pp. 1096-1100.

"Solid-state ion sensors with a liquid junction-free polymer membrane-based reference electrode for blood analysis" by H. J. Yoon et al., Sensors and Actuators B 64 (2000), pp. 8-14.

"Introduction to Microengineering" by Danny Banks, http://www.dbanks.demon.co.uk/ueng/chemsens.html, Apr. 26, 1999.

"The Electrochemical Detection of Oxygen, Nitric Oxide and Ascorbic Acid" *The Bio Currents Research Center*, http://www.mbl.edu/labs/BioCurrents/electrochemical/Electrochemical.html.

"A Beginners Guide to Ion-Selective Electrode Measurements" by Chris C. Rundle BSc, PhD., Nico2000 Ltd, London, UK, Version May 5, 2000, http://www.nico2000.net/Book/Guide1.html.

"The Radiometer™ Product Line" *by Radiometer Medical A/S*.

"Unmatched speed and simplicity at the Point of Care" *by Radiometer Medical A/S*.

"ABL™ 77 Specifications" *by Radiometer Medical A/S*.

* cited by examiner

DISPOSABLE, SELF-ADMINISTERED ELECTROLYTE TEST

CROSS-REFERENCE TO RELATED APPLICATION

This application claims the benefits of and priority to U.S. Provisional Patent Application Ser. No. 60/364,213 filed on Mar. 13, 2002, which is owned by the assignee of the instant application and the disclosures of which are incorporated herein by reference in their entirety.

FIELD OF THE INVENTION

The invention relates generally to the field of electrochemical ion sensors, and more particularly to a disposable, self-administered electrolyte test.

BACKGROUND OF THE INVENTION

Electrolytes, such as sodium, potassium, calcium, and chloride ions, regulate the human body's nervous system, metabolic processes, renal function, vision, cardiac operation, pH balance, and olfactory senses. The body requires a precise balance of electrolytes in intracellular and extracellular fluids to function properly, and through absorption by the intestines or excretion by the kidneys, the body adjusts electrolyte levels accordingly. Neither the intestines nor the kidneys can function, however, if either the electrolytes are not present to be absorbed or are overabundant and cannot be excreted.

Electrolytes may be depleted by excessive sweating, diarrhea, vomiting, or the use of diuretics, and depletion can lead to seizure, coma, or even death. Children are particularly susceptible to the loss of electrolytes during flu or other illness. An otherwise healthy person can experience greater than normal electrolyte levels during dehydration, which can also occur during a workout or as a result of vomiting and diarrhea. More severe dehydration can lead to a weak pulse, rapid breathing, and disorientation. Furthermore, the body's ability to sweat is diminished if fluids are unavailable. Because sweating is the body's primary cooling mechanism, a dehydrated person can easily overheat, which can cause a range of conditions from cramps to heatstroke.

While commercially available sports drinks and pediatric electrolyte supplements are available to replenish both fluids and electrolytes, an individual simply may not recognize his vulnerability or the rapidity with which electrolytes can be depleted as a result of sickness or during strenuous activity.

SUMMARY OF THE INVENTION

The present invention provides a convenient, self-administered electrolyte test that enables the user to recognize an electrolyte imbalance before injury occurs. The test may, for example, be affixed to the label on a bottle of a commercially available sports drink or a pediatric electrolyte supplement. Alternatively, the electrolyte test may be a personal, self-administered electrolyte test available in the pharmacy section of a retail store or distributed by a physician or clinic (similar to, for example, a home pregnancy test or a personal blood/alcohol test). The test may detect the concentration of one or more electrolytes present in a biomedical fluid, such as blood, plasma, serum, urine, saliva, or sweat.

In one aspect, the invention provides a disposable electrolyte test in the form of a substantially flat package. The electrolyte test includes a flat, planar substrate; a sample-receiving region on the substrate; an ion-sensor cartridge in fluid communication with the sample-receiving region; an indicator on the substrate adjacent the sample-receiving region; and circuitry. The circuitry operates the ion-sensor cartridge and the indicator so as to cause display, on the indicator, of an ionic parameter in response to the presence of a sample on the sample-receiving region.

In one embodiment, the circuitry includes a power source (e.g., a battery). The ion-sensor cartridge may include a plurality of ion-selective electrodes. The substrate, electrodes, indicator, and circuitry may be integrated such that the sensor retains a substantially flat, planar profile. The sample-receiving region and the indicator may be located on the one side of the substrate, while the other side of the substrate may include an adhesive facilitating affixation of the ion-sensor cartridge and the circuitry onto a surface. In one embodiment, the substrate, electrodes, indicator, and circuitry are flexible, permitting the sensor to conform and be affixed to a curved surface. A flexible cover may be peelably affixed over the substrate.

In another aspect, the invention provides a method of performing an electrolyte test. The method includes providing an electrolyte test element including a flat, planar substrate, a sample-receiving region on the substrate, an ion-sensor cartridge in fluid communication with the sample-receiving region, and an indicator responsive to the ion-sensor cartridge. The method includes receiving a sample on the sample-receiving region, and operating the ion-sensor cartridge and the indicator so as to cause display, on the indicator, of an ionic parameter of the sample. In one embodiment, the test element includes circuitry and a power source. The ion-sensor cartridge may include a plurality of ion-selective electrodes. In one embodiment, the method includes the step of affixing the test element onto a surface. The substrate, electrodes, indicator and circuitry may be flexible, and the surface may be curved, permitting the test element to be conformed to the surface. In one embodiment, the sample is saliva.

Other aspects and advantages of the invention will become apparent from the following drawings, detailed description, and claims, all of which illustrate the principles of the invention by way of example only.

BRIEF DESCRIPTION OF THE DRAWINGS

The advantages of the invention described above, together with further advantages, may be better understood by referring to the following description taken in conjunction with the accompanying drawings. In the drawings, like reference characters generally refer to the same parts throughout the different views. The drawings are not necessarily to scale, emphasis instead generally being placed upon illustrating the principles of the invention.

DESCRIPTION OF THE ILLUSTRATIVE EMBODIMENTS

Ion-selective electrodes include ion-selective layers, or membranes, that will pass only certain species. Ions can be transported across a membrane by a number of processes, including complex formation, diffusion, and drift. Diffusion is driven by a concentration gradient, drift by a potential gradient. Ion transport can also be driven by other sources of energy, for example thermal conduction, or an active ion pump utilizing chemical energy to transport ions across a cell membrane.

In the case of a sodium ion-selective electrode, two compartments, A and B, are separated by a semi-permeable membrane (e.g., permeable to only sodium). If the initial concentration of sodium ions in compartment A is zero, sodium ions will move from compartment B to compartment A since there is a concentration gradient across the membrane. A potential develops that is proportional to the log of the concentration of sodium in each compartment. This potential difference between the two compartments is described by the Nernst equation:

$$\Psi_A - \Psi_B = -\frac{RT}{zF}\ln\frac{[A]}{[B]},$$

where $\Psi_A$ is the electric potential in compartment A, $\Psi_B$ is the electric potential in compartment B, R is the ideal gas constant, T is the temperature in Kelvin, z is the valence charge of the ion being transported, F is Faraday's constant, [A] is the concentration in the first compartment, and [B] is the concentration in the second compartment.

To assign a meaningful value to the electric potential, it is compared to a reference value acquired from a reference electrode. Therefore, while an ion-selective electrode measures the potential in the compartment that contains, ideally, only the ion of interest, a reference electrode measures the potential outside. The reference electrode includes a coating that is electrically conducting, while not favoring the conduction of any particular ion. Examples of suitable electrodes will be described below.

Figure 1:
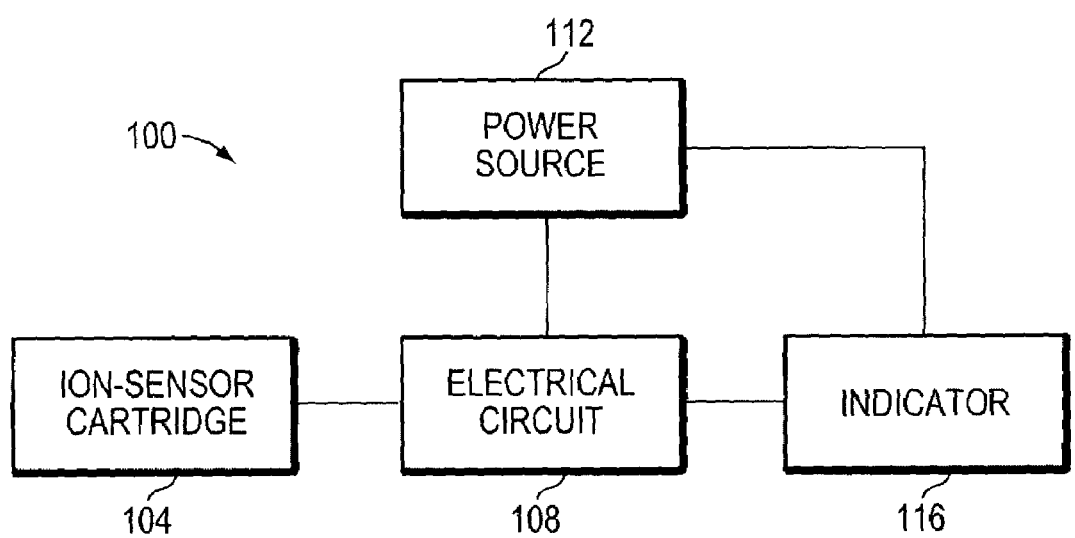
FIG. 1 shows a block diagram of the components of a disposable, self-administered electrolyte test, according to the invention.

A disposable, self-administered electrolyte test may be constructed using ion-specific electrodes. FIG. 1 depicts, in one illustrative embodiment, a block diagram of components of an electrolyte test 100, which includes at least an ion-sensor cartridge 104, an electrical circuit 108, a power source 112 and an indicator 116. The power source 112 supplies electrical power to the electrical circuit 108 and the indicator 116. The ion-sensor cartridge 104 is in electrical communication with the electrical circuit 108.

The electrolyte test 100 provides the ability to detect constituents in a liquid sample. For example, an ion-selective electrode of the invention may be chosen to detect pH (i.e. $H^+$), $Na^+$, $K^+$, $Li^+$, $Ag^+$, $Ca^{2+}$, $Cd^{2+}$, $Ba^{2+}$, $Mg^{2+}$, $Cu^{2+}$, $Pb^{2+}$, $Hg^{2+}$, $Cu^{2+}$, $Fe^{3+}$, ammonium ions ($NH_4^+$), $Cl^-$, $Br^-$, $I^-$, $F^-$, $CN^-$, $OCl^-$, perchlorate ($ClO_4^-$), thiocyanate ($SCN^-$), sulphide ($S^-$), nitrate ($NO_3^-$), nitrite ($NO_2^-$), sulfate ($SO_3^-$), carbonate ($CO_3^-$), bicarbonate ($HCO_3^-$), and/or $S_2O_3^{2-}$. The ion-selective electrodes may be utilized to detect ions by, for example, amperometric, potentiometric, coulombic, conductometric and/or AC analysis techniques. Suitable liquid samples may include saliva, blood, urine, plasma, serum, or sweat.

Figure 2:
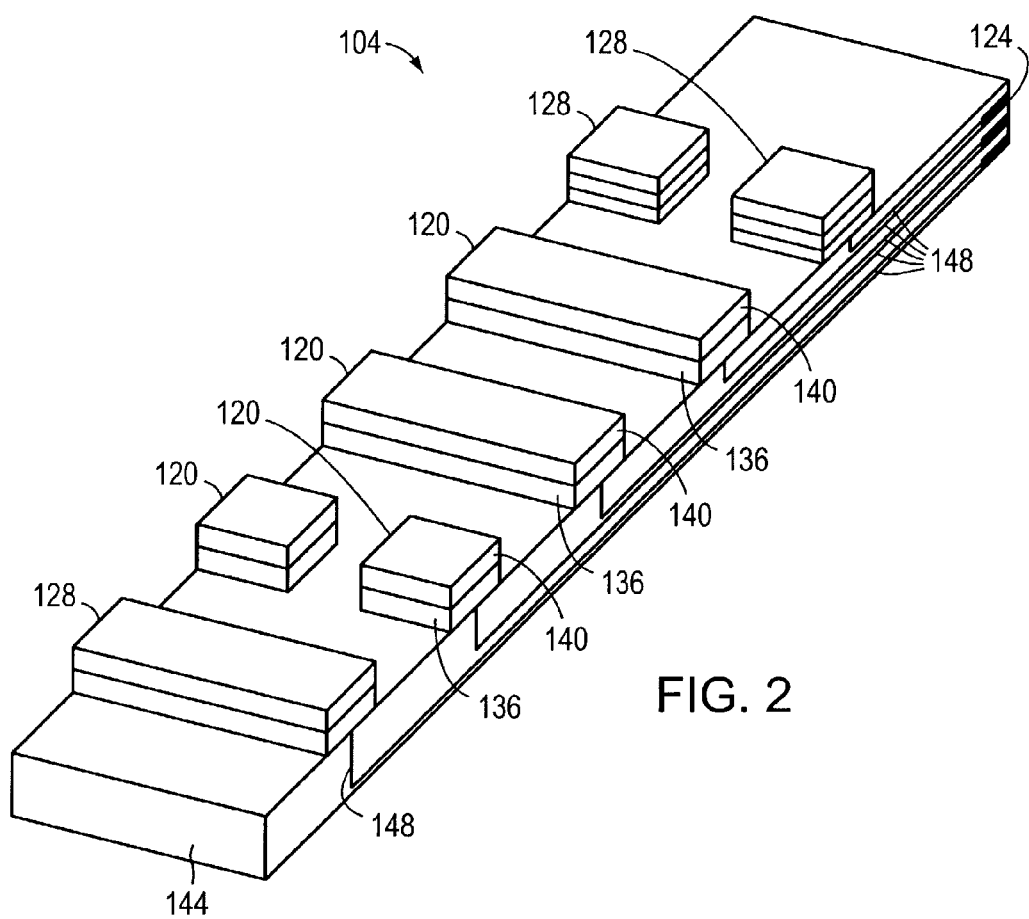
FIG. 2 is a perspective view of an ion-sensor cartridge according to the invention.

FIG. 2 illustrates one embodiment of an ion-sensor cartridge 104. The ion-sensor cartridge includes a plurality of ion-selective electrodes 120, an electrical connection portion 124, and may further include one or more reference electrodes 128. Each ion-selective electrode 120 includes an electrode layer 136 sandwiched between an ion-selective layer 140 and a substrate 144. In one embodiment, the electrode layer includes silver (Ag). Other suitable electrode layers include, but are not limited to, silver/silver chloride (Ag/AgCl), copper (Cu), titanium (Ti), chromium (Cr), gold (Au), platinum (Pt), palladium (Pd), Pd/Ag, platinum black, platinum black/palladium, platinum oxide, iridium (Ir), iridium dioxide ($IrO_2$), and combinations thereof.

In one embodiment, the ion-selective layer 140 includes a doped polymeric material. Suitable polymeric materials include, but are not limited to, polyvinyl chlorides (PVC), polystyrenes, polyacrylates, polycarbonates, polyesters, polyamides, polyurethanes, polyvinylidene chlorides, polyvinyl butyryls, polyvinyl formals, polyvinyl acetates, polyvinyl alcohols, and copolymers of two or more of the above. The dopant may include an ion-selective species such as, for example, a non-dissociable ion-specific, neutral sequestering agent (i.e., an ionophore) or an electrically charged, liquid ion exchanger.

An ionophore is a chemical compound capable of forming a complex with an ion and transporting it through a membrane. The ionophore includes channels that have specific shapes and abilities to bind polar compounds based on the positions of fixed polarities in the molecules in the channel. Ideally, the membrane transports only one ion, but if two ions are similar, a channel designed for one may allow the other also to pass through. The extent to which other ions can diffuse across a membrane is described by the membrane's selectivity coefficient, which can cause deviation from the Nernst equation. The selectivity coefficient is typically measured experimentally, and corrected for by software.

Suitable dopants for a lithium ion-selective electrode include, but are not limited to, N,N'-diheptyl-N,N',5,5'-tetramethyl-3,7-dioxononanediamide, 1,4,7,10-tetraoxyacyclodecane 12-crown-4, and N,N,N',N'-tetraisobutyl-cis-cyclohexane-1,2-dicarboamide. Suitable dopants for a potassium ion-selective electrode include, but are not limited to, valinomycin, dicyclohexano-18-crown-6, bibenzo-18-crown-6, tetraphenyl borate, and tetrakis p-chlorophenyl borate. Suitable dopants for a calcium ion-selective electrode include, but are not limited to, bis(didecylphosphate), bis(4-octylphenylphosphate), and diethyl N,N'-[(4R,5R)-4,5-dimethyl-1,8-dioxo-3,6-dioxaoctamenthylene]bis(12-methylaminododecanoate). Suitable dopants for a sodium ion-selective electrode include, but are not limited to, nonactin, moenensin, N,N',N"-triheptyl-N,N',N"-trimethyl-4,4',4"-popyllinditris-(3-oxabutyramide), bis[(12-crown-4)methyl] dodecylmethylmalonate, and N,N,N',N'-tetracyclohexyl-1,2-phenylenedioxydiacetamide (ETH 2120). Suitable dopants for a hydrogen ion-selective electrode include, but are not limited to, tridodecylamine, N-octadecyloxy-m-chlorophenylhydrazonemeso-oxalonitrile, and N-octadecyloxy-m-chlorphenylhydrazonemeso-oxalonitrile. Suitable dopants for a chloride ion-selective electrode include, but are not limited to, quaternary ammonium chloride, tributyl tin chloride, and Ag/AgCl.

In another embodiment, the ion-selective layer includes a crystalline material or crystalline membrane. For example, for a fluoride ion-selective electrode, the ion-selective layer may include a lanthanum fluoride crystal that has been doped with europium fluoride, which reduces the resistivity of the crystal.

Preferably, the substrate 144 is fabricated from a semiconductor material such as silicon, silicon carbide, gallium arsenide or combinations thereof. Other suitable substrate materials include, but are not limited to, plastics, refractory oxides, and glasses. As described above, the substrate 144 may include one or more reference electrodes 128. Reference electrodes 128 provide a controlled potential for aqueous and biological fluids over a wide range of ionic strengths and compositions. The substrate may include one reference electrode having both an anion and a cation exchange material. For example, a reference electrode may include a solution of 0.6% tridodecylmethylammonium chloride, 0.5% potassium tetrakis (para-chlorophenyl) borate in an aromatic polyurethane dissolved in dimethylformamide (DMF). The solution is applied as a coating and dried in place. Alternatively, the substrate may include one reference electrode for the cation-selective electrodes and another reference electrode for the anion-selective electrodes. Suitable reference electrodes for cation-selective electrodes include, but are not limited to, Ag/AgCl and Ag/AgCl with, for example, a hydrophilic polyurethane, UV-curable polyurethane, and/or UV-curable epoxy. Suitable reference electrodes for anion-selective electrodes include, but are not limited to, Ag/AgCl.

Preferably, the ion-sensor cartridge also contains lead lines 148 that electrically connect one or more ion-selective electrodes 120 and/or reference electrodes 128 to the electrical connection portion 124 of the ion-sensor cartridge 104. The lead lines may be formed (e.g., by affixation or by deposition by, for example, screen printing) on a surface of the substrate, disposed within the substrate, or both. Suitable lead line materials include any sufficiently conductive material to electrically connect an ion-selective electrode or reference electrode to the electrical connection portion of the ion-sensor cartridge. Examples of suitable lead line materials include, but are not limited to, metals such as Ag, Au, Pt, Cu, Ti, nickel (Ni), and layered combinations and alloys thereof, metal oxides such as indium tin oxide (ITO), and conductive polymers such as poly(pyrrole), poly(N-methylpyrrole), poly(3-methylthiopene) and poly(o-anisidine).

Figure 3:
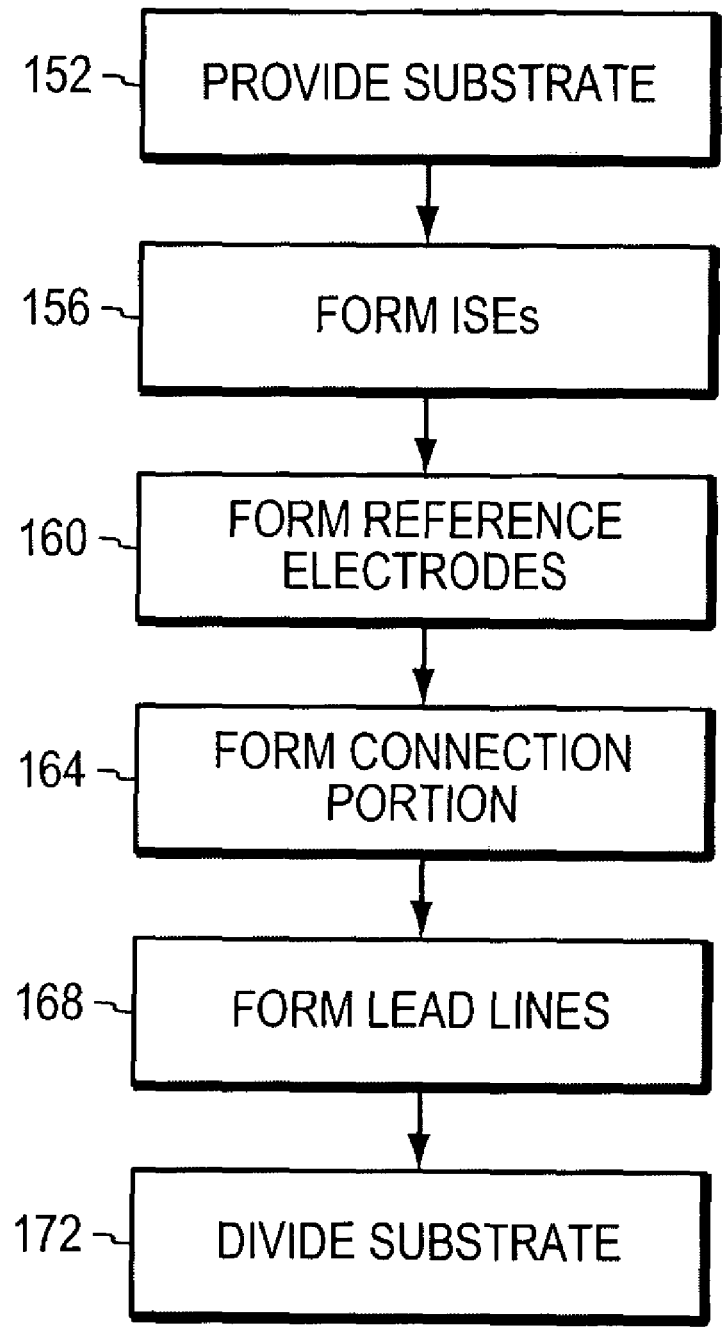
FIG. 3 is a flow diagram that illustrates the steps for fabricating an ion-sensor cartridge, according to the invention.

FIG. 3 shows one embodiment of a way to fabricate an ion-sensor cartridge. A substrate is provided (step 152), and a plurality of ion-selective electrodes (ISEs) are formed on the substrate (step 156). Preferably, the substrate is monolithic and includes silicon, silicon nitride, or borosilicate glass, between about 500 μm to about 2000 μm thick. In addition, the substrate is preferably several times as wide as a strip including a plurality of ion-selective electrodes (e.g., an ion-sensor cartridge) will be. In one embodiment, the ion-selective electrodes are formed by first depositing a stripe of electrode material on the substrate to form an electrode layer, preferably from about 500 Å to about 5 μm thick. The electrode material may be deposited, for example, by screen printing, vapor deposition, electrodeposition, chemical vapor deposition, sputtering, or any other suitable deposition method. Next, an ion-selective material is deposited on the electrode layer to form an ion-selective layer, preferably from about 1 μm to about 5 μm thick. The electrode material may be deposited, for example, by screen printing, mechanical dispensing, or any other suitable deposition method. In one embodiment, the ion-selective material includes a doped polymeric material. This ion-selective material may be prepared, for example, by dissolving a dopant with the polymeric material in a suitable solvent. Suitable solvents include, but are not limited to, DMF and tetrahydrofuran (THF).

In various embodiments, the polymeric material/dopant solution includes a plasticizer. Suitable plasticizers include, but are not limited to, o-nitrophenyl-octylether, dimethylphthalate, bis(2-ethylhexyl)adipate (DOA), bis(2-ethylhexyl)sebacate (DOS), dioctylphenyl-phosphonate, dibutylphthalate, dioctylphthalate, dibutyladipate, hexamethylphosphoramide, diundecylphthalate, and dioctyl sebacate. The polymeric material/dopant solution may be deposited on the electrode layer by, for example, screen printing, pneumatic dispensation, and/or spin casting. A sufficient fraction of solvent is then removed to form an ion-selective layer.

An adhesion promoter may be applied to the substrate or a dielectric layer disposed on the substrate to enhance the adhesion of the ionophore to the substrate or dielectric layer. The dielectric layer maintains electrical isolation between the conductive paths on the surface of the cartridges. The dielectric material may be a spun-on or a deposited organic dielectric such as a polyimide, a photoimagable dielectric, or an inorganic material such as silicon dioxide.

When the substrate material is either glass or silicon, a solution of ethanol, water, and a siloxane may be used. The siloxane preferably includes a functional group at each of the two ends of a long-chain molecule. One end bonds with an OH-terminated substrate (e.g., silicon or glass) and the other bonds to the ionophore. Suitable siloxanes include hexamethyldisiloxane. If the substrate includes a polyurethane-based polymer, then 3-aminopropyltri-methoxysilane or 3-aminopropyltriethoxysilane is generally used. If the substrate includes a polyimide-based dielectric coating, then glutyraldehyde may serve as the adhesion promoter.

The method of fabrication may include a step of forming one or more reference electrodes on the substrate (step 160). In one embodiment, the method forms one or more cation reference electrodes and one or more anion reference electrodes. The cation and/or anion reference electrode may, for example, consist of or include Ag or Ag/AgCl.

In one embodiment, a Ag/AgCl reference electrode is formed by first depositing an electrode layer on the substrate. Second, if the electrode layer is not silver, a silver layer is deposited on the electrode layer. Third, a silver chloride layer is formed by, for example, chlorination by oxidation with a ferric chloride ($FeCl_3$) solution, or by electrolysis by means of a KCl solution. Fourth, the Ag/AgCl layer is coated with an ion-exchange material such as, for example, a doped polymeric material or ion exchange resin. In another embodiment, the formation of a Ag/AgCl reference electrode includes deposition of a solid electrolyte layer on the AgCl layer instead of an ion-exchange material, and coating the solid electrolyte layer with an ion-exchange material.

Referring again to FIG. 3, the method of fabrication may include a step of forming an electrical connection portion on the substrate (step 164) and/or a step of forming lead lines that electrically connect one or more of the ion-selective electrodes and/or reference electrodes to an electrical connection portion (step 168). The electrical connection portion and lead lines may include any conductive material suitable for electrically interconnecting the ion-selective electrodes with a sampler assembly. Suitable conductive materials include, but are not limited to, metals such as Ag, Au, Pt, Cu, Ti, Ni, and combinations and alloys thereof, metal oxides such as indium tin oxide (ITO), and conductive polymers such as poly(pyrrole), poly(N-methylpyrrole), poly(3-methylthiopene) and poly(o-anisidine). Other conductive materials such as silver-filled epoxies may be used. Suitable electrical connection portion and lead line formation techniques include, for example, screen printing, lithography, vapor deposition, or electrodeposition.

It should be recognized that the steps of forming ion-selective electrodes, one or more reference electrodes, an electrical connection portion, and lead lines (steps 156, 160, 164, and 168) may be performed in any order. In addition, two or more of these steps may performed substantially concurrently. For example, where a reference electrode includes an electrode layer, the electrode layers of the reference electrode and one or more ion-selective electrodes may be deposited in the same step. Other combinations and concurrent performances of these steps will be readily apparent to one of ordinary skill in the art from the description of the invention. Subsequent to the ion-selective electrode, reference electrode, electrical connection portion, and/or lead line formation, the substrate is divided into longitudinal strips (step 172) such that at least two or more of the strips include a plurality of ion-selective electrodes (as illustrated, for example, in FIG. 2).

An exemplary ion-sensor cartridge is made using the following procedure. A plurality of ion-sensor cartridges are produced from a single silicon wafer. Titanium is sputtered to form a layer about 1000 Å thick on the polished surface of a four-inch silicon wafer, and then an approximately 0.2 µm thick layer of semiconductor-quality silver is sputtered onto the surface of the titanium. This titanium layer serves to enhance adhesion of the silver layer. A layer of photoresist is then spun onto the silver layer. The photoresist is soft baked, exposed in a pattern and developed to yield a pattern of photoresist on the silver layer (i.e., a metallization pattern). This metallization pattern includes what will eventually become the ion-selective electrodes, the reference electrodes, lead lines and electrical connector portion of the ion-sensor cartridge. The uncovered silver layer is then chemically etched to expose the titanium layer, and the titanium layer is chemically etched to expose the underlying silicon wafer. The remaining photoresist is then removed, and the resultant coated wafer is cleaned (e.g., "descummed" to remove photoresist and/or carbonaceous films) with an oxygen plasma etch.

Photoresist is again spun on, baked, exposed and developed. This photolithographic step is used to protect all the previously patterned components, except for the ion-selective and reference electrode areas. The exposed ion-selective and reference electrode areas are then exposed to a 0.1 M $FeCl_3$ solution for five minutes to convert the exposed areas to AgCl. The photoresist is then removed with a solvent, such as acetone, and the resultant coated wafer cleaned (e.g., descummed) in an oxygen plasma.

A photosensitive polyimide is then spun on the coated surface of the cleaned wafer and soft baked at approximately 55° C. for 70 minutes to produce a final cured thickness of approximately five microns. Subsequently, a second photolithographic step is used to pattern the polyimide to set out the ion sensitive electrode areas, the reference electrode areas and contact pads of the electrical connection portion of the cartridge. The patterned photoimagable polyimide is then developed and rinsed to remove the imaged polyimide from the metal. The resultant coated wafer is then cleaned again with oxygen plasma. The resultant coated wafer is then put through a cure cycle in a nitrogen-purged oven at approximately 300° C. for 60 minutes to cure the remaining polyimide.

A 5% aqueous solution by weight of glutyraldehyde may be used as an adhesion promoter. The array of sensors on the substrate as described above is immersed in the glutyraldehyde solution for approximately two minutes. The substrate is then dried in a desiccator. The ionophores and reference electrode coatings are then selectively deposited onto the AgCl layer of the appropriate ion-selective or reference electrode area by, for example, selective dispensation using a positive displacement pump. For example, a sodium ionophore, having as an active ingredient a one percent concentration of ETH 2120 in a solution of approximately 25% aliphatic polyurethane, 9% PVC and 66% DOA, is dissolved in THF. The solution is then dispensed onto regions where the sodium ion-selective electrodes are formed.

Similarly, a reference electrode coating is dispensed in solution onto one or more reference electrode areas to form reference electrodes. The coating may be a solution of 0.6% tridodecylmethylammonium chloride, 0.5% potassium tetrakis (para-chlorophenyl) borate in an aromatic polyurethane dissolved in THF. The ionophores and reference electrode coatings are then air dried at 50° C. for one hour. The silicon wafer is then divided to produce a plurality of ion-sensor cartridges having, for example, final dimensions of approximately 0.200 inch by 0.050 inch.

Figure 4:
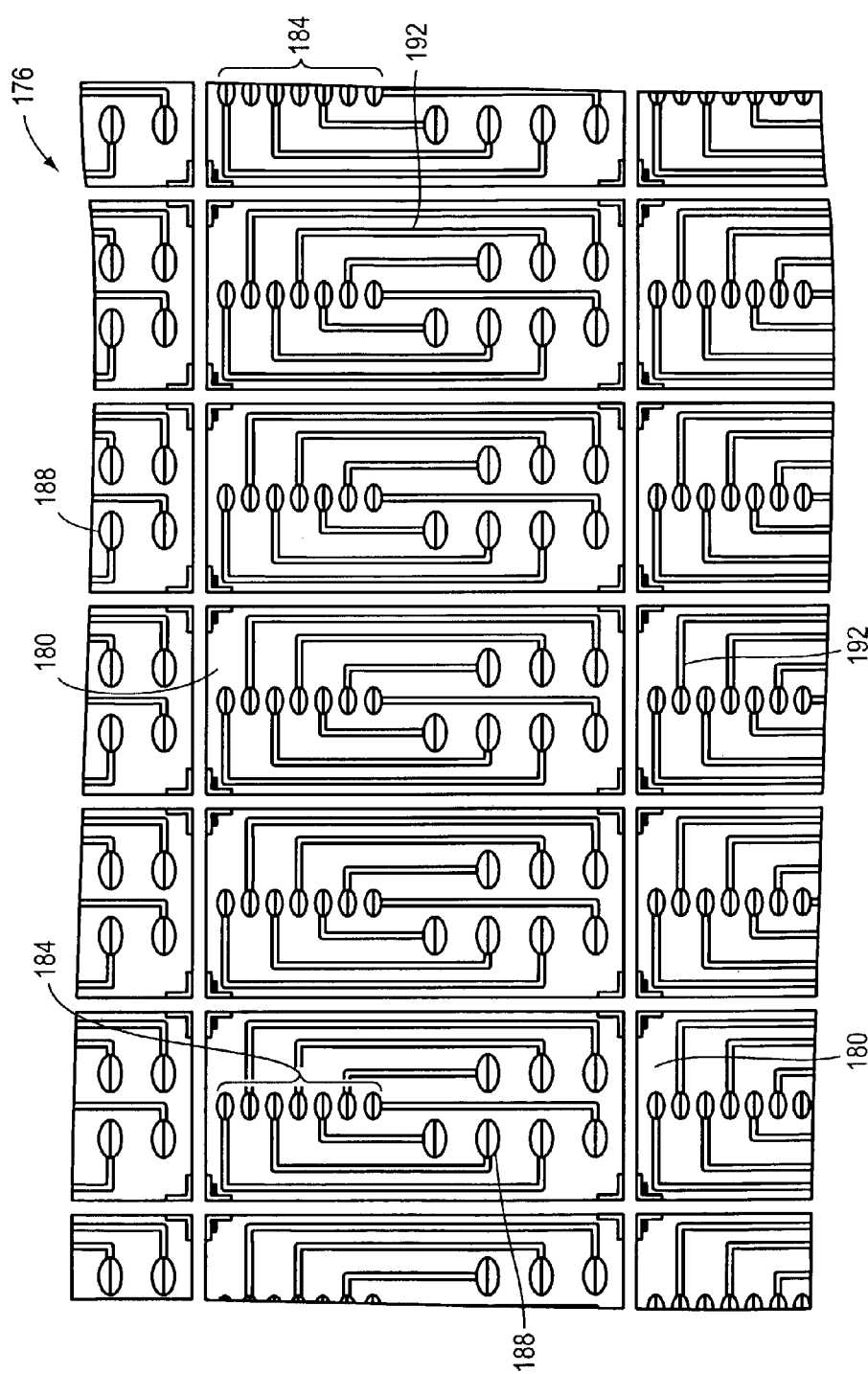
FIG. 4 schematically illustrates a plurality of ion-selective electrode sensors formed on a silicon wafer, according to the invention.

FIG. 4 depicts a portion of a four-inch silicon wafer substrate 176 including a plurality of ion-sensor cartridges 180 with seven electrodes 184. One or more of the seven electrodes are ion-selective electrodes, while the remainder are reference electrodes. Preferably, five of the seven electrodes 184 are ion-selective electrodes, and two of the electrodes 184 are reference electrodes. The wafer substrate 176 is first sputtered with a layer of titanium 1000 Å thick, and is then sputtered with a layer of silver 2000 Å thick. A masking procedure is performed to form the heads of the ion-selective and/or reference electrodes 184 and the contact pads 188. The contact pads 188 facilitate interconnection with a sampler assembly. In one embodiment of an electrolyte test, the contact pads 188 facilitate the electrical connection of the ion-sensor cartridge and the electrical circuit.

The first mask step protects all of the silver except the areas for the electrode heads 184. The silver is then chloridized to form a 1000 Å thick layer of AgCl on top of 1000 Å of silver. The second mask step protects the areas of the electrode heads 184, contact pads 188, and lead lines 192. The silver and titanium are then etched away from the remaining exposed area. The third mask step uses a photoimagable polyimide. The polyimide is removed from the electrode heads 184 and the contact pads 188, and serves as an insulator over the remainder of the wafer substrate 176. Ionophores are deposited over the electrode heads 184, and the wafer substrate 176 is then divided into individual ion-sensor cartridges 180 each with seven electrodes. The individual cartridges 180 may be wire bonded to a larger, easier-to-handle connector, as described above. Preferably, the electrodes have 5 mil diameters, the lead lines are 2 mil wide with at least 2 mil spaces, the contact pads are 10 mil in diameter, and the ion-sensor cartridge is 50 mil wide and 200 mil long.

Figure 5:
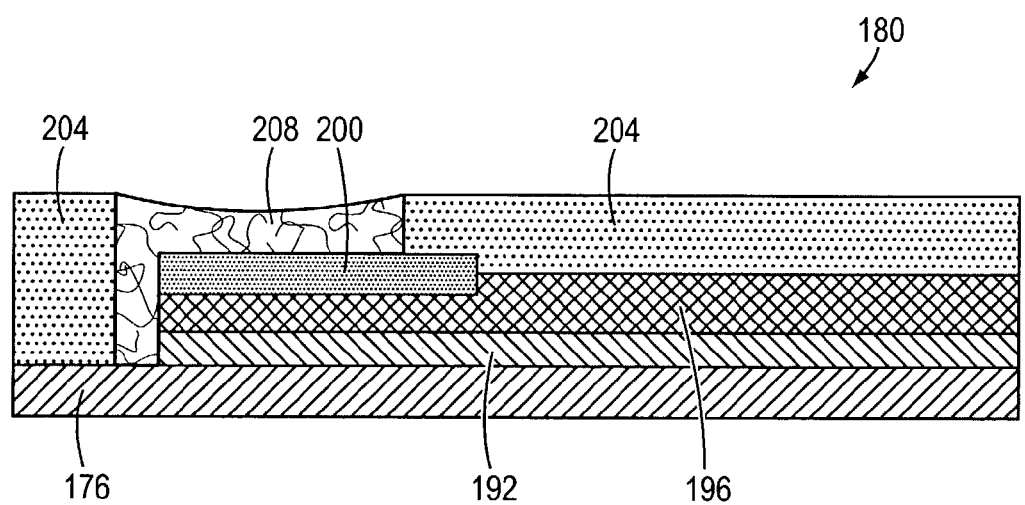
FIG. 5 is a sectional elevation of an ion-selective electrode sensor according to the invention.

FIG. 5 shows a cross-section of the layers formed on an individual ion-sensor cartridge 180. The cartridge 180 includes a substrate 176 on which the titanium layer 192 is sputtered. Preferably, the substrate 176 is silicon. The silver layer 196 is sputtered onto the titanium layer 192. A portion of the silver layer 196 is chloridized to form the AgCl layer 200. Polyimide 204 is then deposited and developed, and then an ionophore 208 is formed.

Figure 6:
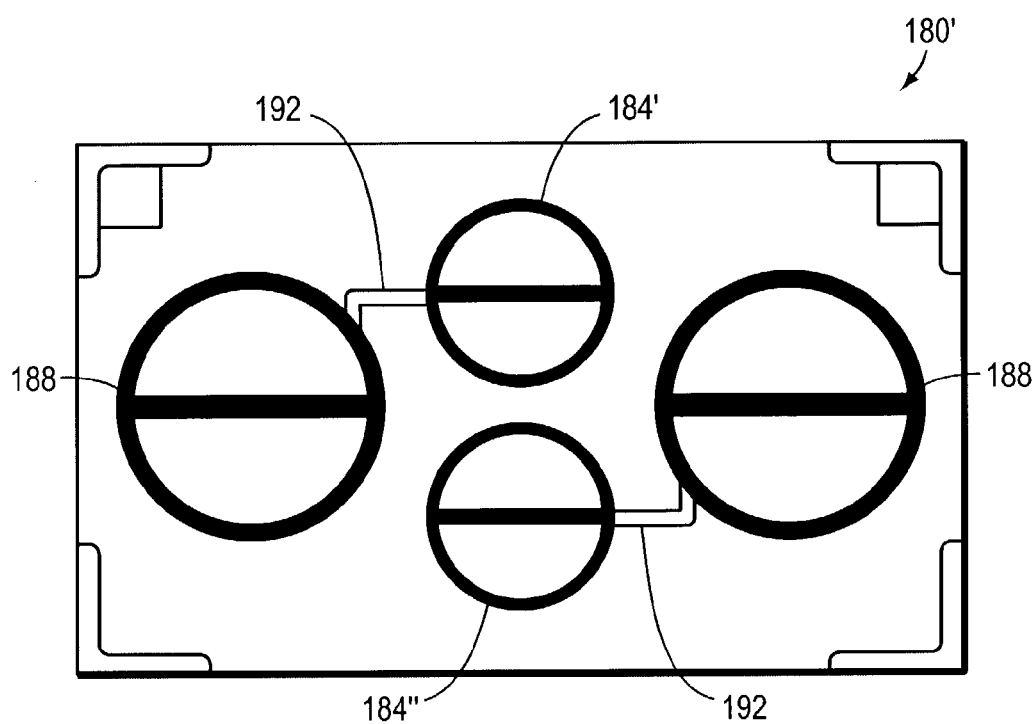
FIG. 6 schematically illustrates an ion-sensor cartridge with two electrodes, according to the invention.

FIG. 6 depicts an illustrative embodiment of an ion-sensor cartridge 180' with two electrodes. One of the electrodes is an ion-selective electrode 184', and the other electrode is a reference electrode 184". The electrodes 184', 184" are electrically connected to contact pads 188 by lead lines 192. The same microfabrication process may be used to make the two-electrode, ion-sensor cartridge 180' as was used for the seven-electrode ion-sensor cartridge 180. The dimensions of the electrodes 184', 184", the contact pads 192, and the lead lines 192 are also the same, but the dimensions of the ion-sensor cartridge 180' are 50 mil by 50 mil. Because the cartridge 180' is smaller than the cartridge 180, a higher yield per four-inch silicon wafer substrate is realized.

Figure 7:
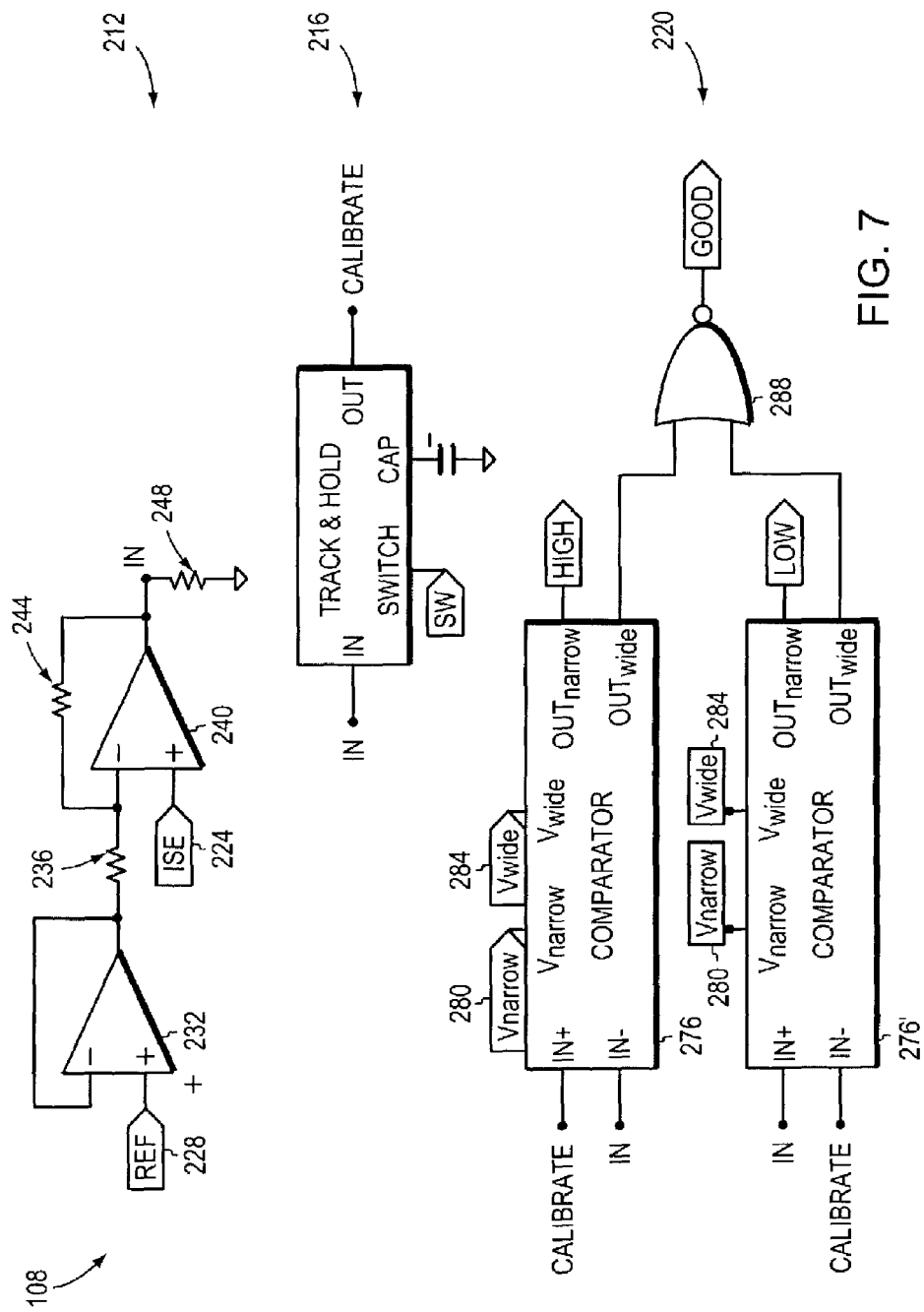
FIG. 7 is a circuit diagram of an input amplifier, a track-and-hold module, and a set of comparators, according to the invention.

To incorporate a disposable electrolyte test on the label of a sports drink or pediatric electrolyte supplement, an electrical circuit 108 may be formed on a circuit board, as a bipolar microchip, or as a CMOS microchip. FIG. 7 shows a block diagram of components of the electrical circuit 108, including an input amplifier stage 212 with high input impedance, a track-and-hold module 216 to calibrate the system, and a set of comparators 220 for the decision making process.

The input stage 212 receives inputs from both the ion-specific electrode 224 and the reference electrode 228. The output of the input stage 212 is a voltage proportional to the difference between the two electrodes 224, 228. A transistor-level operational amplifier (op amp) is used to both buffer the signal and increase gain by a factor of ten before transmitting the signal to the other circuitry. To keep the input impedance high, the electrodes are attached to the gates of transistors, which inhibits current from being drawn from the electrodes. The reference electrode may also be buffered before being connected to the op amp.

Gain is obtained by feeding the output of a first op amp 232 through a first resistor 236 and into the negative terminal of a second op amp 240. Both op amps 232, 240 are in a feedback configuration, and a second resistor 244 is placed in the feedback path of the op amp 240. Preferably, the resistance of the first resistor 236 is 2 kΩ, and the resistance of the second resistor 244 is 20 kΩ. The stability of the circuit 212 is increased by including a load 248 of at least 10 kΩ. The first op amp 232 does not require a load because the second-stage gain resistors 236, 244 also load the first stage.

The op amps 232, 240 operate at low voltage (1.5 V supply) and allow both the input and output to go rail-to-rail (i.e., 0.0 to 1.5 V). An entire decade change in concentration (normal concentration of sodium in saliva is in the range of about 10 to about 25 mM) leads to a change of 60 mV, so a gain of almost ten is supported. This is entirely acceptable if the offset for each electrode is consistent and reproducible, which is not necessarily the case. Therefore, a one-point calibration is used, as described below.

The op amps 232, 240 are not coupled to external sources, although they may be. Instead, current mirrors are used in the output and gain stages to equalize the current through each branch. The op amps do not have a large bandwidth because they operate with DC voltage. The corner frequency may be as low as 10 Hz. While such a small bandwidth may not be ideal for all applications, it has some advantages here. First, the indicators have relatively long transition times, which eliminate the display of erroneous states while the comparator 220 makes a decision. Second, if any 60 Hz noise is picked up from surrounding power sources or lines, it will be reduced by 20 dB relative to the DC signal. Third, the Johnson noise arising from the lead lines connecting the electrodes to the electrical circuit is integrated over a smaller bandwidth, reducing its effect.

Figure 8:
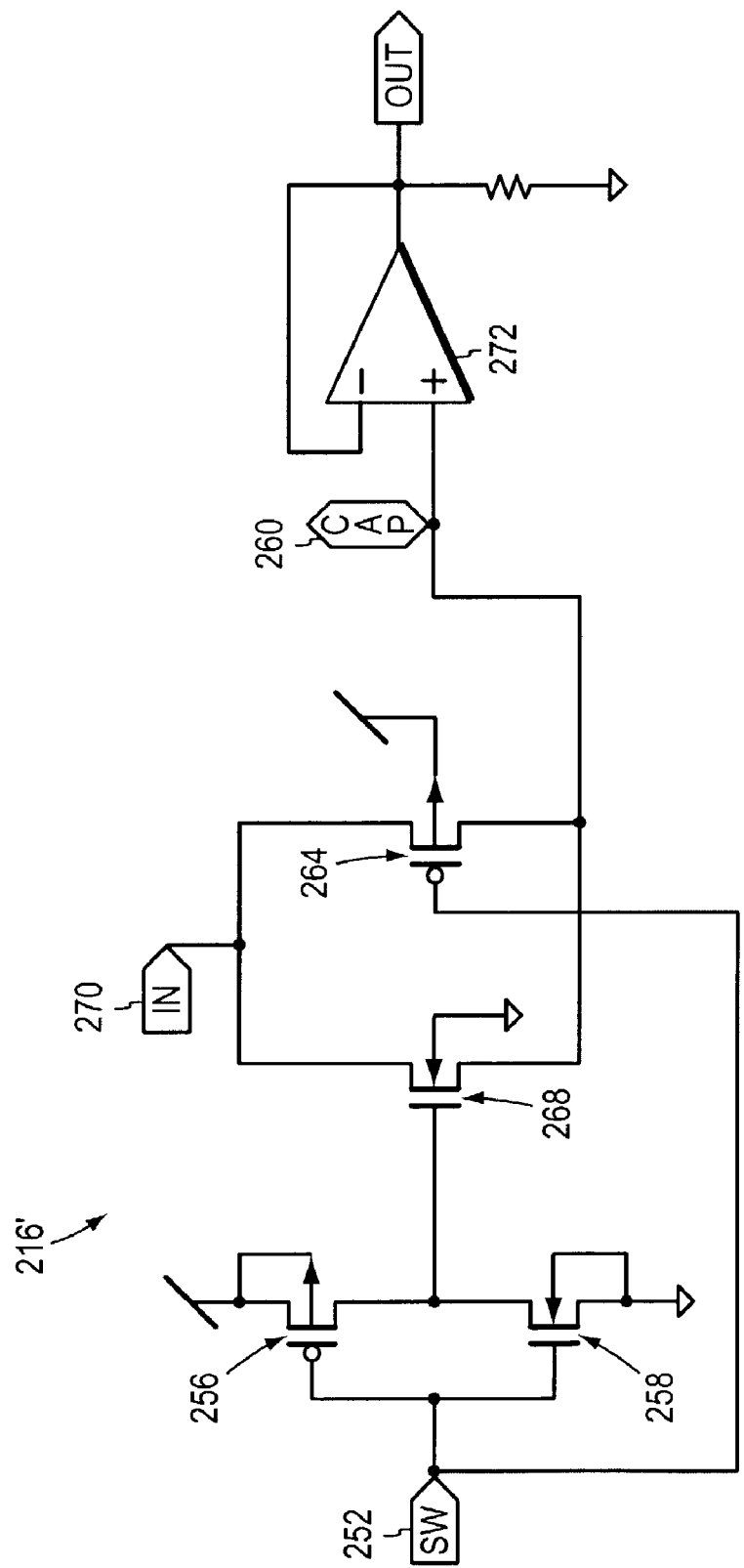
FIG. 8 is a circuit diagram of a track-and-hold circuit according to the invention.

FIG. 8 depicts an illustrative embodiment of a track-and-hold circuit 216' used to calibrate a disposable, self-administered electrolyte test. The switch voltage 252 controls the gates of two complementary transistors 256, 258 that function as the switch for the track-and-hold circuit 216'. The transistors 256, 258 invert the switch voltage 252. A PMOS transistor 264 is connected directly to the switch voltage 252, while a NMOS transistor 268 is connected to the inverted switch voltage 252. The circuit 216' includes a capacitor 260 to hold the voltage used to calibrate the test. When the switch voltage 252 is low (prior to the test being activated), both of the PMOS transistors 256, 264 are "on" and conducting the input signal 270 (i.e., the output signal from the input amplifier 212, see FIG. 7) directly to the positive terminal of an op amp 272. When the switch voltage 252 goes high (when the test is activated), both the transistors turn "off," and the positive terminal of the op amp 272 is then only connected to the capacitor 260.

The capacitor 260 is large enough to hold the calibration voltage for the duration of the test, while not being prohibitive to the size of the electrical circuit 108. Suitable capacitors have a capacitance in the range of about 100 pF to about 400 pF. A preferred range is between about 155 pF and about 270 pF.

Referring back to FIG. 7, the set of comparators 220 make a decision about the user's electrolyte level(s) (e.g., high, low or good). A first comparator 276 outputs when the difference between the input voltage (i.e., the output from the input amplifier 212) and the calibration voltage (i.e., the output from the track-and-hold module 216) is greater than a first user-defined limit. A second comparator 276' outputs when the difference between the calibration voltage (i.e., the output from the track-and-hold module 216) and the input voltage (i.e., the output from the input amplifier 212') is greater than a second user-defined limit. Both limits are dependent on source voltages $V_{narrow}$ 280. While $V_{narrow}$ 280 controls the "high" and the "low" indicators, $V_{wide}$ 284 controls the "good" indicator. If neither output exceeds the user-defined limits, then the output of the comparators 276, 276' is passed to a NOR gate 288, and the "good" indicator is activated.

Figure 9:
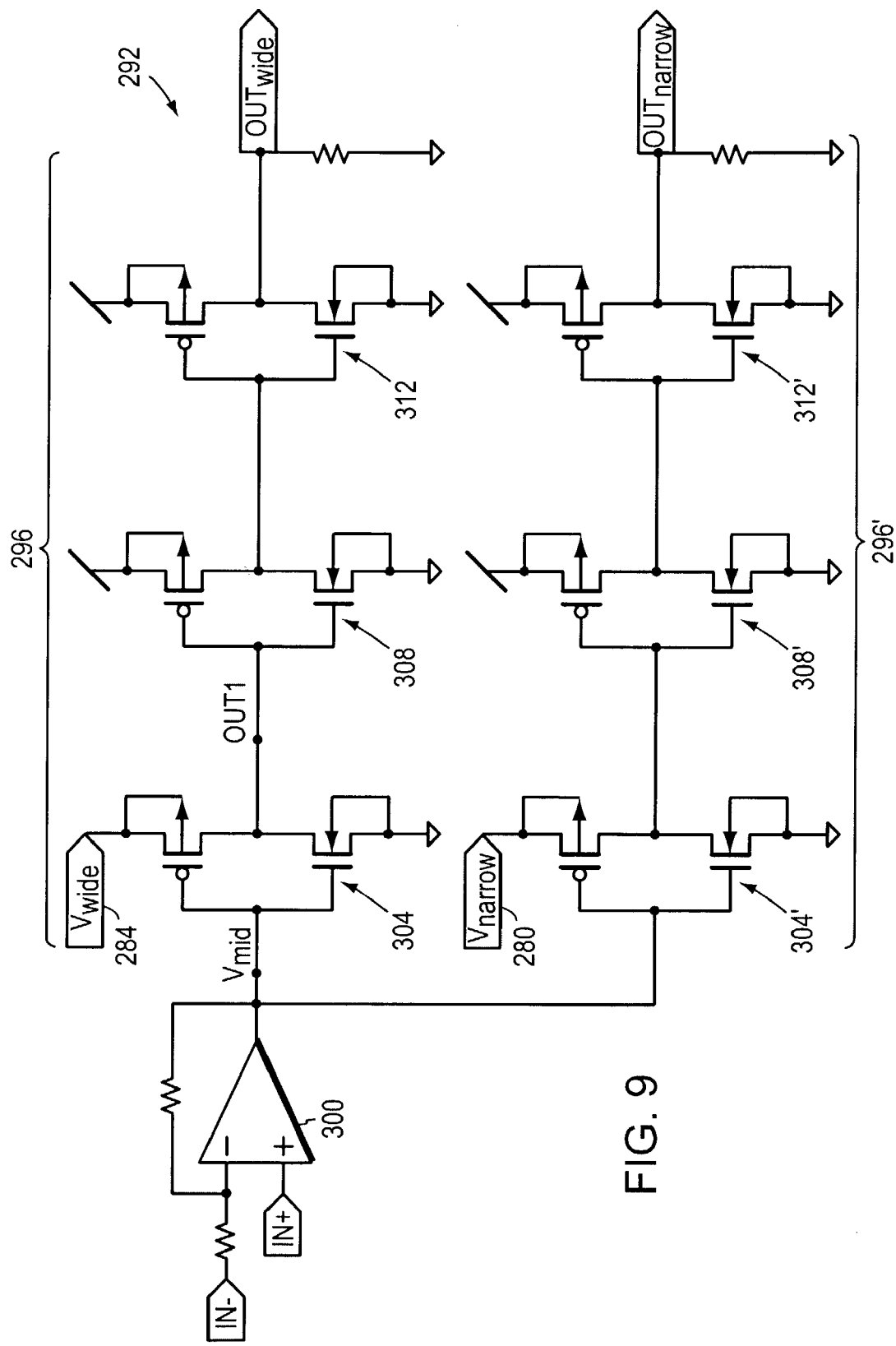
FIG. 9 is a circuit diagram of a comparator according to the invention.

FIG. 9 depicts a representative circuit 292 for the comparators 276, 276'. Two different strings 296, 296' of inverters are attached to the output of an op amp 300. The inverters are MOSFET gates and do not draw current. The source voltage of a first inverter 304, 304' is either $V_{narrow}$ 280 or $V_{wide}$ 284. As described above, the user-defined limits are set by $V_{narrow}$ 280 and $V_{wide}$ 284. For example, a limit of 10 mV may be achieved by setting $V_{wide}$=1.05 V and $V_{narrow}$=1.27 V. Since both the positive and negative comparator blocks use the same voltages for $V_{narrow}$ and $V_{wide}$, only two external sources are required. Alternatively, these two voltages may be supplied on-chip instead of relying on external sources. At least one more inverter 308, 308' is required to return the voltage swing to the full range between power and ground. The third inverter 312, 312' corrects the polarity of the signal.

The ion-selective electrodes may be microfabricated on the same microchip as the electronics using CMOS technology, instead of separate microfabrication processes, one for the ion-sensor cartridge and one for the electrical circuit. This not only reduces the cost, but also conserves wafer "real estate" since the contact pads and lead lines may be eliminated. If the electrodes are fabricated separately, they may be connected directly to the gates of MOSFETs for the purpose of obtaining high input impedance. In addition, ion-selective field effect transistors, or ISFETs, may be used. These electrodes are also built on the gate of a transistor.

The power source 112 (see FIG. 1) of the disposable electrolyte test 100 may be a battery, which has a shelf life comparable to that of the sports drink or pediatric electrolyte supplement to which the test is affixed. A typical shelf life is approximately one to two years. Since the test is disposable, the test does not operate at maximum power for extended periods of time. A typical amount of time to perform an electrolyte test is about one to five minutes. Ideally, the battery is flexible, and the output voltage is 1.5 V.

Figure 10:
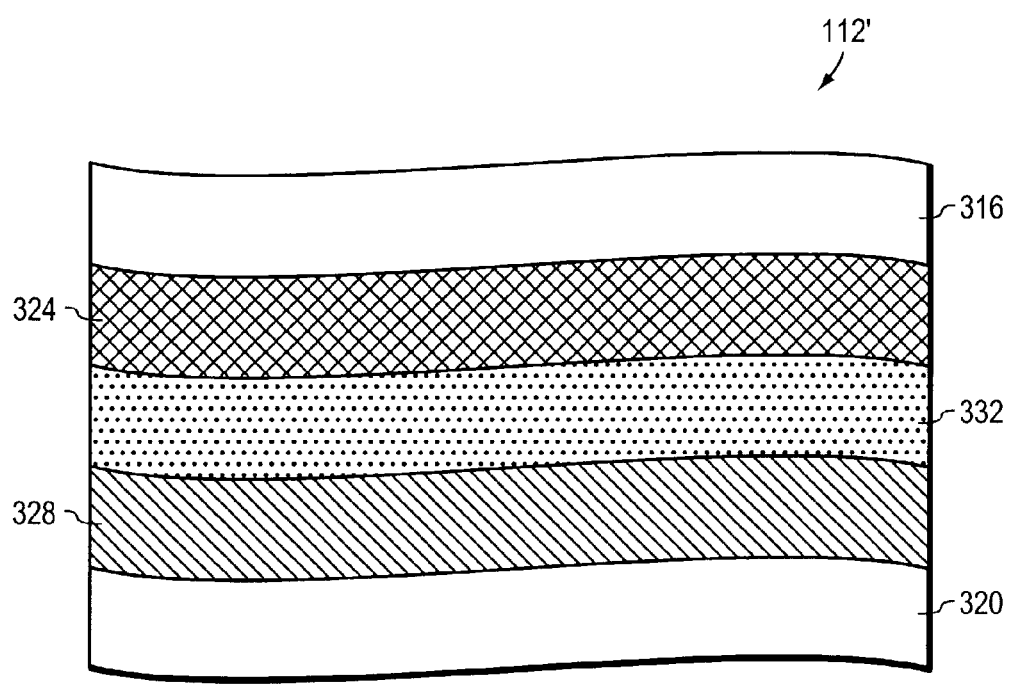
FIG. 10 is a sectional elevation of a battery useful in connection with the invention.

Power Paper Ltd. (Tel Aviv, Israel) manufactures one suitable battery. The chemicals used in Power Paper's battery are a combination of zinc and manganese dioxide. The battery may be printed using silkscreen technology onto almost any surface, including paper or flexible plastic. FIG. 10 depicts an illustrative embodiment of a suitable battery 112'. The battery 112' includes five printed layers including collectors 316, 320 on the top and the bottom, the anode 324, the cathode 328, and the electrolyte core 332. A one-square-inch printed battery provides 1.5 V for 15 mAh, is about 0.5 mm thick, and has a shelf life of up to about two and a half years.

The indicator 116 (see FIG. 1) presents the decision of the set of comparators to the user. The circuitry described above drives three separate indicators, which desirably are easily distinguishable by the user. The power requirement of the indicator is within the capacity of the battery and the driving power of the controlling circuitry. The indicator is also flexible, durable, and inexpensive.

A suitable indicator is a NANOCHROMICS display, available from Ntera Ltd. (Dublin, Ireland). The indicator uses electrochromic ink that changes color in response to an electric potential. The diameter of the particles of the electrochromic ink is 5-20 nm, and therefore they can be printed using a conventional ink-jet printer. The indicator can change state in 0.1 seconds. The ink is either clear or white in its off-state and upon the application of 1.2 V turns blue, green, or black depending on the specific ink. The indicator holds its state until an opposite potential is applied. Because this is a type of ink that can be printed onto plastic or paper, it can be made flexible and conformable. In order to change state, 3 mC of charge is required for each square centimeter of display.

Figure 11B:
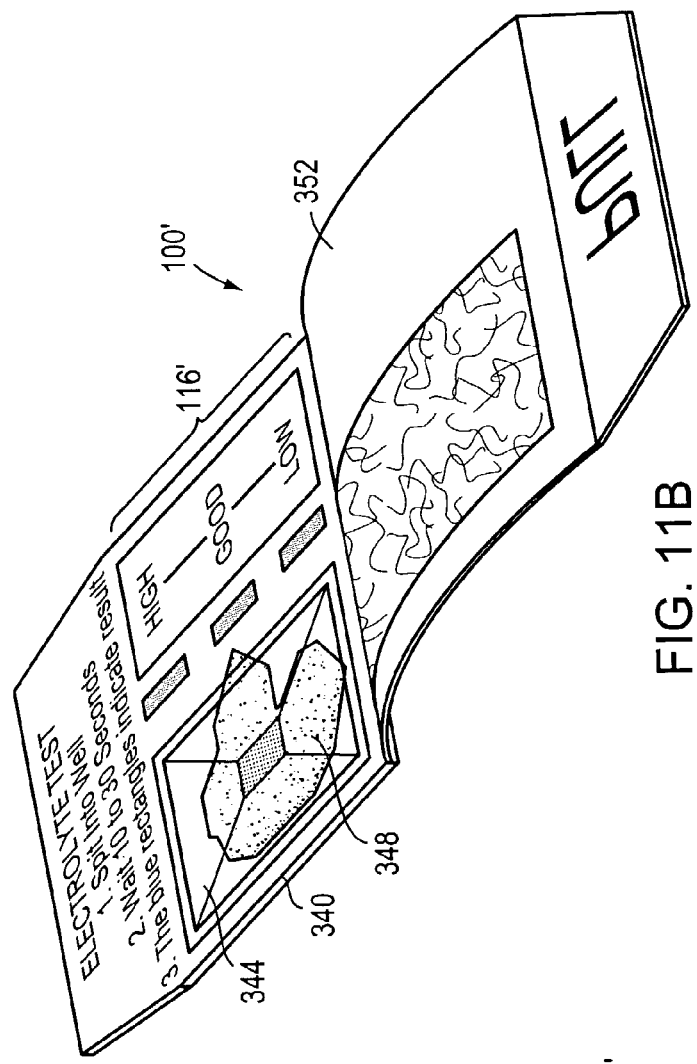
FIG. 11B is a perspective view of a disposable electrolyte test.
Figure 11A:
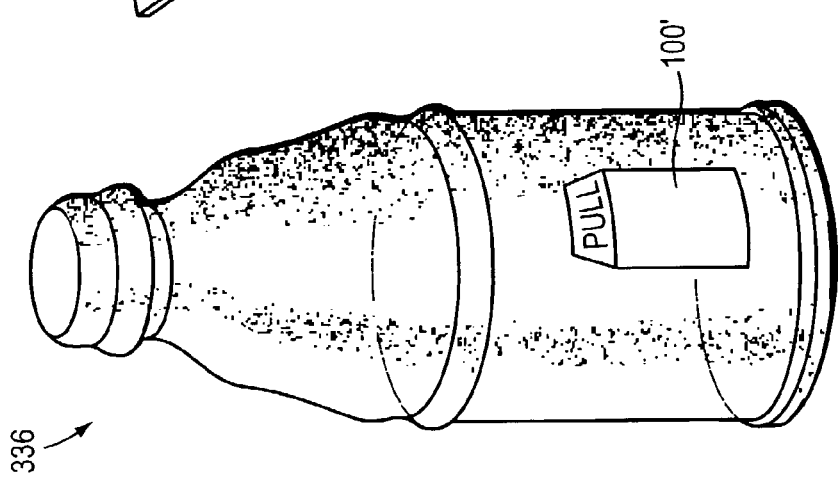
FIG. 11A is a perspective view of a disposable electrolyte test affixed to a bottle, according to the invention.

FIG. 11A depicts one illustrative embodiment of a disposable electrolyte test 100' affixed to the side of a bottle 336. The test 100' is a substantially flat package. FIG. 11B shows the disposable electrolyte test 100' peeled away from the bottle 336 and opened. The test 100' includes a flat, planar substrate 340, on which a sample-receiving region 344 and an indicator 116' are affixed. The sample-receiving region 344 includes or is in fluid communication with an ion-sensor cartridge, as detailed above. The electrical circuit (also described above) for operating the ion-sensor cartridge, which includes ion-selective electrodes, is embedded within or behind the substrate 340 and causes display on the indicator 116'. The display on the indicator 116' is dictated by an ionic parameter sensed in a sample 348 on the sample-receiving region 344. The electrolyte test 100' may include a flexible cover 352, which can be peeled away from the substrate 340 to reveal the sample-receiving region 344 and the indicator 116'.

The electrolyte test 100' is preferably constructed from flexible materials so that it may be conformed to the side of the bottle 336. In one embodiment, the sample-receiving region 344 and the indicator 116' are formed on the top surface of the substrate 340, and the ion-sensor cartridge and electrical circuit are affixed to or formed on the underside of the substrate 340. Alternatively, the ion-sensor cartridge and electrical circuit may be encapsulated within the substrate 340 and a second substrate adhered to the substrate 340. In addition, the electrical circuit may include the power source, or may be in electrical communication with the power source.

While the indicator shown in FIG. 11B includes three rectangles for display, the rectangles may display five different ranges of an ionic parameter, e.g., electrolyte level. For example, the normal, human saliva concentration range of sodium ion is from about 10 mM to 25 mM. The three indicators may be configured to have five states corresponding to sodium concentration as follows:

Very High (top indicator), greater than 50 mM $Na^+$
High (top and middle indicators), 25 mM to 50 mM $Na^+$
Good (middle indicator), 10 mM to 25 mM $Na^+$
Low (middle and bottom indicators), 5 mM to 10 mM $Na^+$
Very Low (bottom indicator), less than 5 mM $Na^+$.

The electrolyte test described above need not be affixed to the side of a bottle. It may be suitably packaged for sale at a retail store or distribution by a physician or clinic. For example, the power source may be a replaceable battery and the ion-sensor cartridge may also be replaceable. The indicator can indicate a range of electrolyte levels, as described above, or provide a numerical display of the electrolyte level.

While the invention has been particularly shown and described with reference to specific illustrative embodiments, it should be understood that various changes in form and detail may be made without departing from the spirit and scope of the invention as defined by the appended claims.

What is claimed is:

1. A disposable electrolyte test in the form of a substantially flat package, the electrolyte test comprising:
   a. a flat, planar substrate;
   b. a sample-receiving region on the substrate;
   c. an ion-sensor cartridge in fluid communication with the sample-receiving region, the ion-sensor cartridge comprising an ion-selective layer for passing only certain species of a sample to an electrode layer;
   d. an indicator on the substrate adjacent the sample-receiving region, wherein the indicator comprises a plurality of indicator elements for indicating a concentration level of an electrolyte within the sample;
   e. circuitry for operating the ion-sensor cartridge and the indicator so as to cause display, on the indicator, of an ionic parameter in response to the presence of the sample on the sample-receiving region; and
   f. a flexible cover affixed over the substrate so as to be unsealable therefrom and to thereby expose the sample-receiving region,
   wherein the disposable electrolyte test is configured to conformably affix to a curved surface of a fluid container.

2. The electrolyte test of claim 1 wherein the circuitry comprises a power source.

3. The electrolyte test of claim 2 wherein the power source is a printed battery.

4. The electrolyte test of claim 1 wherein the ion-sensor cartridge further comprises a plurality of ion-selective electrodes.

5. The electrolyte test of claim 4 wherein the substrate, electrodes, indicator and circuitry are integrated such that the electrolyte test retains a substantially flat, planar profile.

6. The electrolyte test of claim 5 wherein the substrate has first and second sides, the sample-receiving region and the indicator being located on the first side of the substrate, the second side of the substrate comprising an adhesive facilitating affixation of the ion-sensor cartridge and the circuitry onto a surface.

7. The electrolyte test of claim 1 wherein the ionic parameter is an electrolyte level.

8. The electrolyte test of claim 1 wherein the ion-selective layer comprises a semi-permeable membrane.

9. The electrolyte test of claim 8 wherein the semi-permeable membrane is adapted to be permeable to at least one of $H^+$, $Na^+$, $K^+$, $Li^+$, $Ag^+$, $Ca^{2+}$, $Cd^{2+}$, $Ba^{2+}$, $Mg^{2+}$, $Cu^{2+}$, $Pb^{2+}$, $Hg^{2+}$, $Cu^{2+}$, $Fe^{3+}$, ammonium ions ($NH_4^+$), $Cl^-$, $Br^-$, $I^-$, $F^-$, $CN^-$, $OCl^-$, perchlorate ($ClO_4^-$), thiocyanate ($SCN^-$), sulphide ($S^-$), nitrate ($NO_3^-$), nitrite ($NO_2^-$), sulfate ($SO_3^-$), carbonate ($CO_3^-$), bicarbonate ($HCO_3^-$), and $S_2O_3^2$.

10. The electrolyte test of claim 1 wherein the ion-selective layer comprises a doped polymetric layer.

11. A method of performing an electrolyte test, the method comprising:
  a. providing an electrolyte test element comprising a flat, planar substrate, a sample-receiving region on the substrate, an ion-sensor cartridge in fluid communication with the sample-receiving region, an indicator responsive to the ion-sensor cartridge, and a flexible cover over the substrate so as to be unsealable therefrom and to thereby expose the sample-receiving region;
  b. receiving a sample of saliva on the sample-receiving region; and
  c. operating the ion-sensor cartridge and the indicator so as to cause display, on the indicator, of an ionic parameter of the sample, wherein the electrolyte test element is configured to conformally affix to a curved surface of a fluid container.

12. The method of claim 11 wherein the test element further comprises circuitry and a power source.

13. The method of claim 12 wherein the power source is a printed battery.

14. The method of claim 11 wherein the ion-sensor cartridge comprises a plurality of ion-selective electrodes.

15. The method of claim 11 further comprising the step of affixing the test element onto a surface of the fluid container.

16. The method of claim 11 wherein the ionic parameter is an electrolyte level.

* * * * *